United States Patent [19]

Gradeff et al.

[11] Patent Number: 4,599,201
[45] Date of Patent: Jul. 8, 1986

[54] PROCESS FOR PREPARING CERIC CARBOXYLATES

[75] Inventors: Peter S. Gradeff, Pottersville; Vincent J. Charte, East Windsor, both of N.J.

[73] Assignee: Rhone-Poulenc, Inc., New Brunswick, N.J.

[21] Appl. No.: 637,940

[22] Filed: Aug. 6, 1984

Related U.S. Application Data

[63] Continuation of Ser. No. 367,310, Apr. 12, 1982, abandoned.

[51] Int. Cl.$^4$ .................. C01F 17/00; C11C 1/00
[52] U.S. Cl. .................. 260/414; 260/429.2; 423/21.1; 423/263; 556/16
[58] Field of Search ............... 260/414, 429.2; 423/21.1, 263

[56] References Cited

U.S. PATENT DOCUMENTS 4,231,893  11/1980  Woodhead ................ 423/263
4,285,868  8/1981   Heiba et al. .............. 549/321

OTHER PUBLICATIONS

*Comprehensive Inorganic Chemistry*, vol. 4, Pergamon Press Ltd., 1973, pp. 97–101, Moeller, Therald, "The Lanthanides: Oxid. State +4".

*J. Amer. Chem. Soc.*, vol. 93, No. 1. Jan. 13, 1971, pp. 995–999, Heiba, E. I., "Oxidation by Metal Salts. VIII. The Decomposition of Ceric Carboxylates in the Presence of Olefins and Arom. Hydrocarbons".

*Primary Examiner*—Charles F. Warren
*Assistant Examiner*—Elizabeth A. Flaherty

[57] ABSTRACT

A process is provided for preparing ceric carboxylates which comprises oxidizing cerous carboxylate with aqueous hydrogen peroxide in a two-phase system comprising an aqueous phase of hydrogen peroxide having a pH of at least 6 and an organic phase comprising a solution of cerous carboxylate in a water-immiscible hydrocarbon solvent at a temperature at which the reaction proceeds but below the temperature of rapid decomposition of hydrogen peroxide, thereby converting cerous to ceric ion and forming a solution of ceric carboxylate in the hydrocarbon solvent; heating the reaction mixture at a temperature at which any ceric-hydrogen peroxide complexes present are decomposed; and separating the organic phase containing ceric carboxylate from the aqueous phase of the reaction mixture.

22 Claims, No Drawings

PROCESS FOR PREPARING CERIC CARBOXYLATES

This is a continuation of application Ser. No. 367,310, filed Apr. 12, 1982, and now abandoned.

Heavy metal soaps such as cobalt, lead, vanadium, zirconium, nickel and other naphthenates are widely used as accelerators or driers to speed up the drying and curing of oil-based varnishes and paints. They are also used as additives in plastics, in flame-retardant compositions, silicones, and fuels.

Cerium soaps are known to have drying action but have not come into wide use because they are expensive to prepare. Recently they also have been proposed as additives in fuels, flame-retardant compositions and plastics and silicones and have other potential applications. The cerium soaps described in the literature are cerous soaps. To our knowledge there is only one description in the literature of ceric soaps or their preparation, and that is by B. L. Kalsotra et al *Transition Metal Chemistry*, 1, 158–161 (1976), who state that a good deal of work has been carried out on cerous carboxylates "but there is no reference in the literature to the preparation of ceric carboxylates". The paper deals with the preparation and characterization of ceric carboxylates by the reaction of $H_2CeCl_6$ with $HCO_2H$, a mixture of (MeCO)$_2$O, EtCO$_2$H, n-PrCO$_2$H and 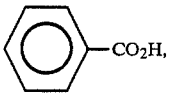—CO$_2$H, respectively:

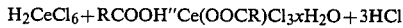

$H_2CeCl_6 + RCOOH''Ce(OOCR)Cl_3xH_2O + 3HCl$

The carboxylates prepared by this method contain three chlorine atoms, as shown above. Attempts by Kalsotra et al to prepare ceric carboxylates by the reaction of dipyridinium ceric hexachloride $(C_5H_6N)_2CeCl_6$ with sodium salts of fatty acids, analogous to the preparation of ceric cyclopentadienyl and ceric indenyl compounds, failed.

There are however cerium soaps on the market that are actually a mixture of cerous and ceric carboxylates; these are cerium naphthenates containing from 30% to 50% ceric naphthenate. The method for their preparation has not been divulged; they are being manufactured in France.

The method used for preparing heavy metal soaps depends on the reactivity of the particular metal or derivatives thereof. The processes most commonly used are:

(a) anion exchange, displacing an inorganic anion by carboxylate anion, carried out by adding a base to a well agitated aqueous solution of a metal inorganic salt in the presence of a solution of the desired carboxylic acid in an appropriate water-immiscible solvent;

(b) precipitation of the metal soap from aqueous solutions of the metal salts with alkali soaps;

(c) fusion of metal oxides, hydroxides or salts with organic acids or esters; and (d) direct reaction of finely-divided metals in heated organic acids.

Process-wise, methods (a) and (b) are the easiest to carry out, and are usually also the most economical. They are applicable to cerium as well as to many other metals. Any available soluble common cerous salt such as cerous nitrate or chloride can be used in method (a) to prepare cerous soaps. Theoretically, by analogy to cerous soaps, water-soluble ceric ammonium nitrate or ceric sulfate can be used to prepare ceric soaps. There is no literature reference showing that this has ever been done, however. The problem is that ceric ammonium nitrate and ceric sulfate, the only commercially available water-soluble ceric salts, are prohibitively expensive. This is perhaps one reason why only cerous and no ceric soaps are described in the literature.

When the solid metal soap is desired, process (b) is most suitable, and is applicable to cerium. Any available soluble cerium salt such as cerous nitrate or chloride can be used to prepare cerous soaps in solid form. While theoretically the water-soluble ceric salts such as ceric ammonium nitrate or ceric sulfate could be used, and perhaps are used in preparing the available mixed cerous/ceric naphthenates, ceric soaps are either liquids or waxy substances, and would be hard to isolate from the reaction mixture.

Moreover, it is also prohibitively expensive to prepare ceric soaps according to method (b), because the only available soluble inorganic ceric salts are the expensive ceric ammonium nitrate and ceric sulfate.

Ceric hydroxide is of low reactivity and solubility, and not suitable for either method (a) or (b).

In accordance with the present invention, the use of expensive ceric ammonium nitrate or ceric sulfate is avoided by starting with the corresponding cerous soap, oxidizing the cerous soap to the ceric soap with aqueous hydrogen peroxide.

The problems in handling and recovery of ceric soap from the reaction mixture are eliminated by carrying out the oxidation with aqueous hydrogen peroxide in a two-phase system comprising an aqueous phase of hydrogen peroxide having a pH of at least 6 and an organic phase comprising a solution of cerous carboxylate in a water-immiscible hydrocarbon solvent at a temperature at which the reaction proceeds but below the temperature of rapid decomposition of hydrogen peroxide, thereby converting cerous to ceric ion and forming a solution of ceric carboxylate in the hydrocarbon solvent. Then, when reaction is complete, the reaction mixture is heated at a temperature at which any ceric-hydrogen peroxide complexes are decomposed, and the organic phase then separated from the aqueous phase of the reaction mixture. The ceric carboxylate is normally used in the solution as prepared and can be recovered from the organic phase by any desired procedure, such as by solvent distillation at low temperature and pressure.

The reaction is theoretically capable of quantitatively converting cerous to ceric carboxylate. It is not however necessary for most commercial purposes to effect a complete conversion. The ratio of $Ce^{+4}$ produced over the total cerium present can be varied as desired from 1% up to 100%.

The usefulness of only 1% $Ce^{+4}$ in $Ce^{+3}$ carboxylate solutions can be appreciated by the unexpected reduced viscosity of the $Ce^{+3}/Ce^{+4}$ carboxylate solution which otherwise could pose problems. Both cerous and ceric carboxylate are chemically equivalent as a source of cerium for reactions where cerium is desired, as in driers or accelerators. However, organic solvent solutions of ceric carboxylates have a much lower viscosity than organic solvent solutions of cerous carboxylates at like cerium concentrations, and the reduction in viscosity is already marked when the total cerium is 1% ceric. It is thus suitable for many purposes to convert as little as 1% of the cerous cerium to ceric. However, it is normally desirable to convert from 30% to 60% and preferably from 50% to 95% of the cerous to ceric cerium, for applications where higher $Ce^{+4}$ content is sought.

The cerous carboxylate can be used directly as a starting material, in solution in the water-immiscible hydrocarbon solvent, and the aqueous hydrogen peroxide solution having a pH of at least 6 combined with this solution in forming the two-phase reaction system. The cerous carboxylate can also be formed in situ from a cerous compound and a carboxylate compound, for example, an inorganic cerous salt such as cerous nitrate or cerous sulfate, and the carboxylic acid with alkali, or the carboxylic acid salt, in which case alkali is not necessary. The cerous carboxylate forms in situ as an intermediate, but in any event the product is ceric carboxylate, in solution in the solvent.

When cerous carboxylate is used as a starting material, the procedure is referred to herein as Method I, and when a cerous compound and a carboxylate compound are used as a starting material, the procedure is referred to herein as Method II. These two procedures, while similar in principle, are rather different in execution, process-wise, and therefore will be considered separately.

Method I, since it involves cerous carboxylate as the starting material, can also include the preparation of cerous carboxylate from an inorganic cerous salt and a carboxylic acid, and in this event the reaction mixture can be used directly in the hydrogen peroxide oxidation, without separation of cerous carboxylate solution from the aqueous layer. This is the most economical way to apply the process, and is therefore preferred.

While the most practical and economical way to produce the ceric soaps is by integrating an oxidation step in the process of making cerous soaps, the oxidation can also be applied to a solution of any cerous soap in a hydrocarbon solvent by adding an aqueous solution of hydrogen peroxide. For instance, any commercial cerous carboxylate solution can be mixed with an aqueous solution of hydrogen peroxide, whereupon the oxidation will take place. Excess carboxylic acid, preferably as the ammonium or alkali metal salt, can also be added.

METHOD I

For synthesis of cerous carboxylate, method (a) above can be used. A base such as alkali metal, for example sodium or potassium, hydroxide or ammonium hydroxide is added to a two-phase system containing water-immiscible solvent and a well-agitated aqueous solution of a soluble cerous salt such as cerous nitrate, cerous chloride, or cerous sulfate and the corresponding carboxylic acid, all in at least stoichiometric amount but preferably using an excess of the acid. Cerous carboxylate obtained in this manner is then extracted from the aqueous reaction mixture with a water-immiscible hydrocarbon solvent in which it is soluble, and which advantageously can be present at the time of addition of the base, thus forming a two-phase system already in this stage, or at the end of the precipitation of cerous carboxylate from the aqueous phase. The organic phase of cerous carboxylate dissolved in hydrocarbon solvent can then be separated from the aqueous phase, but this is not necessary.

Three moles of carboxylic acid is stoichiometrically required per mole of $Ce^{+3}$ salt to make the $Ce^{+3}$ carboxylate. Theoretically, one extra mole of acid is needed if all $Ce^{+3}$ is to be converted to $Ce^{+4}$ in the form of ceric carboxylate. The fact is that the oxidation proceeds well at less than the theoretical amount of acid. This is an indication that the $Ce^{+4}$ carboxylate produced by the process contains other functions such as —OH or other bondings.

The base that is used in carrying the method (a) for preparing cerous soaps can be sodium or potassium hydroxide, carbonate or bicarbonate, or ammonium hydroxide. The amount of base is important; at least the stoichiometric amount for the cerium is required in order to convert all cerium into solvent-soluble cerium carboxylate, and to adjust pH to at least 6, and preferably higher than 7, prior to the oxidation with hydrogen peroxide.

Hydrogen peroxide is added as an aqueous solution shortly after the addition of the base has been completed, and prior to the separation of the two layers. Preferably, the pH of the reaction mixture prior to the $H_2O_2$ addition is above 6. While the order of combining the reactants can be varied, the addition of $H_2O_2$ should be last, for better results.

The reaction mixture is kept under vigorous agitation while the aqueous solution of hydrogen peroxide is being added. The reaction begins at room temperature and the reaction mixture rapidly develops a reddish dark brown color. Hydrogen peroxide is known to form colored water-soluble complexes with inorganic ions and probably the same is occurring in this case with ceric ion. In the process of the invention, the cerium carboxylate/hydrogen peroxide system forms a dark colored organic solvent solution due to the complex, which upon heating decomposes by releasing $H_2O_2$. Therefore, after a short period of time during which some of the hydrogen peroxide oxidizes $Ce^{+3}$ to $Ce^{+4}$ and the rest becomes immobilized in forming the said complex, the temperature of the reaction mixture is brought to from 60 to 75° C., to destroy ceric-$H_2O_2$ complexes, whereupon the color lightens to a permanent yellow orange, indicating their decomposition.

The amount of hydrogen peroxide added can vary considerably, according to the extent desired of the conversion of cerous to ceric, from 5% to above 90%. A 100% conversion is difficult to obtain as there appears to be some degree of reduction of $Ce^{+4}$ to $Ce^{+3}$, which in some cases, depending on the carboxylate ion, is responsible for a drop in and thus a limitation upon the maximum $Ce^{+4}$ content. Small amounts of $H_2O_2$ can also be used, which will result in a lesser conversion of cerous to ceric. A small conversion, ranging from 1% to 5%, could be desirable for some applications. The degree of conversion depends also on the nature of the carboxylic acid and the impurities present. The degree of conversion of cerous to ceric is greater in the case of neodecanoic acid than for naphthenic acid, for example.

To achieve a high conversion of cerous to ceric, two or more additions of hydrogen peroxide followed each time by a heating-cooling sequence to decompose ceric-$H_2O_2$ complexes may be required, depending upon the carboxylate anion. In the case of some carboxylates, one addition of $H_2O_2$ is enough to raise ceric to over 90%. With other carboxylates, in order to reach 90%, two or three additions of $H_2O_2$ are needed, as for instance with ceric naphthenate. One reason for this is that the mixture sold as naphthenic acid is itself oxidizable by ceric, and this secondary reaction consumes ceric, converting it to cerous and holding down the ceric content.

The amount of carboxylic acid as already indicated should be more than stoichiometrically required for the cerous soap, i.e., 3 moles per g atom of cerium. The corresponding ceric soap made in accordance with this invention may contain some OH or other bonding, which is acceptable for many of the applications. Quite often, cerous soap solutions contain an excess of the corresponding carboxylic acid. It is preferable to use about 4 moles of carboxylic acid, so as to have the amount stoichiometrically required for the ceric soap that is to be made. More than 4 moles of acid can be used, if desired.

METHOD II

In accordance with this method, cerous ion in the reaction medium is oxidized by adding an aqueous solution of hydrogen peroxide:
(1) into an aqueous solution of alkali carboxylate and prior to the addition of the aqueous solution of cerous salt, or
(2) into an aqueous solution of the inorganic cerous salt solution either (a) prior to the mixing with the alkali carboxylate solution, or (b) at a controlled rate during the mixing with the alkali carboxylate solution. The presence of an organic solvent during the reaction is preferable, to extract the ceric soap as it is formed.

The amount of hydrogen peroxide is not critical, and can vary from less than the stoichiometric amount required to a large excess. Normally, an excess is preferred, because of the tendency of the ceric ion to form complexes with the $H_2O_2$. After the mixing of the alkali carboxylate and the cerous salt has been completed, more hydrogen peroxide can be added to increase the ceric content, if desired. It may be necessary in some cases to heat the solution to from 65° to 70° C. to destroy the colored ceric-$H_2O_2$ complex, prior to adding more $H_2O_2$.

The addition of $H_2O_2$ is preferably done at room temperature, but the temperature can extend up to 70° C., with the penalty of a correspondingly less efficient reaction, because of loss of $H_2O_2$. At the conclusion of the reaction, the reaction mixture is heated at 60° to 75° C., to decompose the ceric-$H_2O_2$ complex, and destroy all excess $H_2O_2$.

In both methods, the yield can be improved by extracting the aqueous phase with organic solvent, and combining this with the organic phase, when the ceric carboxylate is sparsely soluble in water.

The process of the invention can be used for conversion of any cerous soap which can be dissolved in a water-immiscible hydrocarbon solvent, in a sufficient amount to permit the reaction to proceed. The process is of particular application and commercial interest to the preparation of ceric naphthenate, ceric 2-ethylhexoate, and ceric neodecanoate, which are therefore preferred, but it can of course be applied for the preparation of any desired ceric carboxylate salt of any aliphatic or cycloaliphatic saturated or unsaturated carboxylic acid or mixture thereof having from about seven to about eighteen carbon atoms, starting from the corresponding cerous carboxylate.

Exemplary carboxylic acids providing carboxylate anion include capric, 2-ethyl hexoic, caprylic, lauric, myristic, stearic, palmitic, oleic, linoleic, linolenic, ricinoleic, napthenic, methyl cyclohexanoic, methyl cyclohexenoic, cycloheptanoic, and the fatty acid mixtures derived from natural fats and oils, such as coconut oil fatty acids, tallow fatty acids, lard fatty acids, corn oil fatty acids, linseed oil fatty acids, tung oil fatty acids, rapeseed oil fatty acids, cottonseed oil fatty acids, fish oil fatty acids, soyabean oil fatty acids and safflowerseed oil fatty acids.

If the cerous carboxylate is not available, the process of the invention is combined with its preparation as a first step, using a water-soluble cerous salt such as cerous ammonium nitrate, cerous nitrate, cerous sulfate or cerous acetate with the free carboxylic acid in the stoichiometrically equivalent amount as starting materials.

Any water-immiscible liquid hydrocarbon solvent in which the cerous soap can be dissolved to form the organic phase of the reaction mixture can be employed, including aliphatic, cycloaliphatic and aromatic hydrocarbon solvents having from about six to about fourteen carbon atoms such as, for example, petroleum ethers, which are composed of paraffinic hydrocarbons, cycloaliphatic hydrocarbons, and mixtures thereof, hexane, heptane, octane, nonane, decane, dodecane, tetradecane, cyclohexane, cycloheptane, cyclopentane, cyclooctane, cycloheptene, cyclohexene, cyclooctene, benzene, toluene, p-cymene, psuedo-cumene, the xylenes, mesitylene, ethylbenzene, 1,2,3-trimethylbenzene, tetramethylbenzene, propylbenzene, isopropylbenzene, the dipropylbenzenes and the diisopropylbenzenes.

The following Examples in the opinion of the inventors represent preferred embodiments of the invention.

EXAMPLE 1

In a four-necked three-liter round-bottom flask equipped with a rapid-stirring mechanical stirrer, thermometer, condenser and addition funnel were placed 146.8 g of aqueous cerous nitrate solution (23.86% cerous), 0.250 mole, 190 g neodecanoic acid, 1.011 moles, and 358.9 g Amsco 140 (a petroleum ether solvent composed of 42% naphthenic hydrocarbons and 58% paraffinic hydrocarbons). Aqueous ammonium hydroxide, 1035 g, 1.006 moles, was added dropwise to the well-agitated mixture of neodecanoic acid, cerous nitrate solution and petroleum ether. Following completion of the addition of the ammonium hydroxide over a two hour period, 26.0 g of 30% aqueous hydrogen peroxide, 0.23 mole, was added in an equal weight, 26 g, of water. The reaction mixture turned a deep brown, and after forty minutes of reaction heating was begun to 70° C., to decompose the $Ce^{+4}/H_2O_2$ complexes, and continued for an additional twenty minutes. In the course of the decomposition, the reaction mixture turned orange, then bright yellow. After cooling, the reaction mixture separated into two layers; a clear orange upper organic layer and an almost clear yellow lower aqueous layer.

The layers were separated, and washed with 200 g of water. The organic layer was diluted with 300 g hexane, and the water azeotroped out, after which the hexane was distilled. The $Ce^{+4}$ in the residue (581.9 g) was 94% of the total cerium.

EXAMPLE 2

To the reaction vessel described in Example 1 was added 29.4 g aqueous cerous nitrate solution assaying 23.79% Ce (0.05 mole), 38.0 g neodecanoic acid (0.20 mole), and 72.6 g Amsco 140. The aqueous ammonium hydroxide 167.2 g (0.16 mole) was added dropwise to the well-agitated mixture of neodecanoic acid, aqueous cerous nitrate and petroleum ether solvent over ten minutes. There was then added the aqueous hydrogen peroxide, 5.2 g, 30% $H_2O_2$, together with an equal weight, 5.2 g, of water. The mixture turned dark brown, and the temperature began to rise. After forty minutes of reaction, heating was begun to 78° C. over ten minutes, to decompose the $Ce^{+4}/H_2O_2$ complex, whereupon the reaction mixture became orange-yellow, and then yellow.

The reaction mixture was cooled to 40° C. and the mixture separated into two layers, an upper pearlescent yellow organic layer, and a lower slightly yellow aqueous layer.

The wet hexane solution was azeotroped dry. The cool solution was filtered through Supercel filter aid and the cake washed with hexane. The collected orange shiny solid ceric neodecanoate was 0.26 g. After distillation of the hexane from the organic layer, 119.6 g of product was recovered, assaying 5.09% $Ce^{+4}$.

EXAMPLE 3

In a reaction flask was added 176.4 g aqueous cerous nitrate solution assaying 23.79% cerium (0.3 mole), 169.2 g neodecanoic acid (0.9 mole), and 208.8 g Amsco 140, and stirring begun. Aqueous ammonium hydroxide, 1044.4 g (1.009 moles) was added dropwise to the well-agitated mixture over a period of one hour at 22° to 23° C. At the conclusion of this period the pH was 7. Hydrogen peroxide was then added (0.2 mole, as 30% solution) together with an equal amount of water over a few minutes. The mixture was allowed to react for twenty minutes, and then the temperature was brought to 70° C. and held there for twenty minutes to decompose the $Ce^{+4}/H_2O_2$ complex. The reaction mixture was then cooled to 40° C., whereupon it separated into two layers; an upper organic layer, which was viscous and tan, in the form of an emulsion, and a lower aqueous layer which was colorless and clear.

To the mixture was added 100 g of hexane. The layers were then separated. The aqueous layer was extracted with two portions of 130 g each of hexane and the organic washings were then combined with the organic layer, the water azeotroped out from the organic layer, after which the hexane was distilled off. The residual 443.1 g Amsco solution was assayed at 1.3% $Ce^{+4}$.

EXAMPLE 4

Into a 500 ml round-bottom flask equipped with a rapid stirrer and a dropping funnel was charged 29.4 g aqueous cerous nitrate solution assaying 23.86% Ce (0.05 mole), 29.3 g 2-ethylhexoic acid (0.20 mole) and 81 g of Amsco 140. Aqueous ammonium hydroxide solution, 205.7 g, 2.6% $NH_3$, was then added dropwise over forty minutes. At the end of the addition the pH of the reaction mixture was 7.5. The organic layer was slightly viscous, and the aqueous layer was clear. There was then added 5.22 g hydrogen peroxide, 30% $H_2O_2$, with vigorous stirring. A dark brown color formed almost at once, and the organic layer became less viscous. Stirring was continued for forty-five minutes. Upon completion of this reaction time, heating to 70° C. was then begun, to destroy the unreacted $Ce^{+4}/H_2O_2$ complexes. After 75° C. was reached, this temperature was maintained for thirty minutes. The dark brown color disappeared, resulting in an orange, slightly yellow oil and an aqueous layer.

The reaction mixture was cooled with ice to 20° C. There was then added 5 g ammonium hydroxide solution, followed by 1.53 g 30% hydrogen peroxide solution, and the reaction mixture was then stirred for thirty minutes. The mixture was then heated to 70° C. and held at this temperature for thirty minutes.

The reaction mixture was then cooled to 20° C., at which point the pH was 7.0. There was then added 1.53 g hydrogen peroxide as a 30% $H_2O_2$ solution. The reaction mixture was stirred for one hour, and then heating to 70° C. begun. The reaction mixture was held at 72° C. for thirty minutes, and then cooled to 20° C. in an ice water bath.

The organic layer was separated from the aqueous layer, and washed with two portions of 25 g each of water. The weight of the organic layer was 110.0 g. There was then added 100 g hexane, and refluxing begun to remove the water. Hexane was then removed under 40 to 80 mm at a pot temperature of 42° to 62° C. The product was a yellow-green oil, 114.6 g, 5.17% $Ce^{+4}$.

EXAMPLE 5

In the reaction system of Example 4 there was placed 29.4 g aqueous cerous nitrate solution assaying 23.86% cerium (0.05 mole), 50.5 g (0.20 mole) naphthenic acid and 59.3 g Amsco 140. Stirring was begun, and aqueous ammonium hydroxide solution 170.0 g (0.170 mole) was then added dropwise over a period of forty minutes. Next was added 3.1 g $H_2O_2$, 30% $H_2O_2$ solution (0.0327 mole) to the vigorously stirred reaction mixture. A dark brown color formed. Stirring was continued for forty-five minutes and the mixture then heated to 75° C. to destroy the $Ce^{+4}$/hydrogen peroxide complexes, and held at this temperature for thirty minutes. The mixture was then cooled in a water/ice bath to 20° C., whereupon it separated into two layers. The organic layer was removed, 100 g hexane added, and the mixture then heated to reflux. Refluxing was continued, azeotroping out the water. The remaining hexane was then distilled under low pressure, yielding an oily material which was dried over sodium sulfate. Total cerium by analysis was 3.07%, of which 70% or 2.15% was $Ce^{+4}$. Weight 214 g.

EXAMPLE 6

| Charges | Amount | Mwt. | % | Moles | Molar Ratio |
| --- | --- | --- | --- | --- | --- |
| $Ce(NO_3)_3$ solution | 29.4 g | 140.12 | 23.86 $Ce^{+3}$ | 0.050(Ce) | 1.00 |
| Amsco 140 | 61.6 g | | | | 1232 g/mole Ce |
| Naphthenic acid | 48.2 g | 240.8 | | 0.200 | 4.0 |
| NaOH solution | 156 ml | 40 | 0.980$\underline{N}$ | 0.153 | 3.06 |
| $H_2O_2$ solution | 4.8 g | 34 | 32.7 | 0.046 | 1.84 |

A 500 ml three-necked round bottomed flask was equipped with mechanical stirrer, thermometer, pH electrode and dropping funnel.

The cerium solution, naphthenic acid and Amsco 140 were combined and stirred vigorously while the NaOH solution was added over 2.5 hours. The peroxide was added in an equal volume of water over five minutes causing a deep red color. The mixture was left stirring for twenty hours. The mixture was heated to 70° C. for one-half hour, cooled and then the organic layer was assayed to give 73% ceric.

EXAMPLE 7

| Charges | Amount | Mwt. | % | Molar Ratio |
|---|---|---|---|---|
| Ce(NO$_3$)$_3$ solution | 29.4 g | 140.12 | 23.86 Ce | 1 |
| Amsco 140 | 81.0 g | — | | |
| Octoic acid | 29.3 g | 144.2 | 98.3 | 4 |
| NaOH solution | 165.4 ml | 40 | 0.980 N | 3.24 |
| H$_2$O$_2$ solution | 4.8 g | 34 | 32.9 | 1.84 |

A 500 ml three-necked round bottomed flask was equipped with mechanical stirrer, thermometer, pH electrode and dropping funnel.

The cerium solution, octoic acid and Amsco were combined and stirred vigorously while the NaOH solution was added over two hours.

The hydrogen peroxide solution (4.8 g) was added and the mixture was stirred seventeen hours. The mixture was heated to 70° C. for one-half hour, cooled, then assayed to give 70% ceric. A second portion of 3.4 g peroxide was added followed by overnight stirring and short heating to give 91% ceric. The two layers split very quickly and cleanly.

EXAMPLE 8

There were mixed 2.0 g cerous ethyl hexoate solid with 50.0 g of Amsco 140 and stirred until approximately 80% dissolved. H$_2$O$_2$ solution (0.38 g of a 10% aqueous solution) was added and the mixture stirred to obtain a red-orange solution which was allowed to stand for two hours and then placed in a 70% bath for thirty minutes to decompose CeH$_2$O$_2$ complexes. The color became lighter, whereupon the mixture was allowed to cool and settle.

Titration with ferrous ammonium sulfate solution indicated 24% Ce$^{+4}$ total cerium.

EXAMPLE 9

There was added 2.46 g cerous naphthenate solid moles to 50.0 g Amsco 140 and then stirred and heated to 60° C. to obtain a solution which was cooled to 25° C. H$_2$O$_2$ solution (0.58 g of a 10% aqueous solution) was added and the mixture stirred for five minutes, placed in a 70° C. bath for thirty minutes and allowed to cool to 25° C. The upper layer was sampled and titrated with ferrous ammonium sulfate, indicating 46.2% Ce$^{+4}$ total cerium.

EXAMPLE 10

Ethyl hexoic acid (1.0 g) was added to 2 g of solid cerous ethyl hexoate. Upon heating and addition of 50 g of Amsco all went into solution. Hydrogen peroxide (10% solution) 0.60 g was added at room temperature, and after five minutes the reaction was heated to 70° C. and then cooled. A second portion of 0.6 g of H$_2$O$_2$ was added, at room temperature and heated again to 70° C. Analysis indicated that 1.24% of total Ce was ceric.

EXAMPLE 11

There was placed 4.4 g 2-ethyl hexoic acid in a flask. There were added 4.0 g of 30% NaOH solution, followed by 0.57 g of 30% H$_2$O$_2$ solution, stirred and 5.9 g Ce(NO$_3$)$_3$ solution added to obtain an orange solution which solidified after three minutes. 10.5 g Amsco 140 was added to make an aqueous solution, which was stirred for five minutes and then placed in a 70° C. bath for thirty minutes. The solution was allowed to cool and organic layers sampled for titration.

$$\text{w/w \%} \frac{\text{ceric}}{\text{Total Ce}} = 12\%$$

Repeated additions of H$_2$O$_2$ increased the amount of ceric.

EXAMPLE 12

| Charges | Wt. | Assay % | Wt 100% | Moles |
|---|---|---|---|---|
| Cerous 2-ethylhexoate | 2.0 | 24.0 | 0.48 g Ce | 0.0034 |
| 2-Ethylhexoic acid | 1.0 | 98.3 | 0.9030 | 0.0070 |
| Amsco 140 | 50.0 | | 50.0 | |
| H$_2$O$_2$ | 1.16 | 10 | 0.1166 | 0.0034 |

Cerous 2-ethylhexoate and 2-ethylhexoic acid were combined. 50.0 g Amsco 140 and 0.58 g H$_2$O$_2$ (10% w/w) were added, stirred five minutes and heated to 70° C. over thirty minutes and then cooled.

$$\text{w/w \%} \frac{\text{ceric}}{\text{Total Ce}} = 46.4\%.$$

0.58 g H$_2$O$_2$ (10% w/w) was added a second time, stirred five minutes, and heated at 70° C. over thirty minutes and then cooled.

$$\text{w/w \%} \frac{\text{ceric}}{\text{Total Ce}} = 67.8\%.$$

Having regard to the foregoing disclosure, the following is claimed as the patentable and inventive embodiments thereof:

1. A process for preparing ceric carboxylates which comprises oxidizing a cerous carboxylate of an organic carboxylic acid selected from the group consisting of aliphatic and cycloaliphatic saturated and unsaturated carboxylic acids and mixtures thereof having from about seven to about eighteen carbon atoms with aqueous hydrogen peroxide in a two-phase system comprising an aqueous phase of hydrogen peroxide having a pH of at least 6 and an organic phase comprising a solution of cerous carboxylate in a water-immiscible hydrocarbon solvent at a temperature at which the reaction proceeds but below the temperature of rapid decomposition of hydrogen peroxide, thereby converting cerous to ceric ion and forming a solution of ceric carboxylate in the hydrocarbon solvent; heating the reaction mixture at a temperature at which any ceric-hydrogen peroxide complexes present are decomposed; and separating the organic phase containing ceric carboxylate from the aqueous phase of the reaction mixture.

2. A process according to claim 1 in which the cerous carboxylate is used directly as a starting material, in solution in the water-immiscible hydrocarbon solvent, and the aqueous hydrogen peroxide solution combined with this solution in forming the two-phase reaction system.

3. A process according to claim 1 in which the cerous carboxylate is prepared from an inorganic cerous salt and a carboxylic acid by the addition of a base, and the reaction mixture used directly in the hydrogen peroxide oxidation, without separation of cerous carboxylate.

4. A process according to claim 3 in which an alkali metal hydroxide, carbonate or bicarbonate is added to a well-agitated aqueous solution of a water-soluble inorganic cerous salt, and the corresponding carboxylic acid in an at least stoichiometric amount, and extracting cerous carboxylate from the aqueous reaction mixture with a water-immiscible hydrocarbon solvent in which it is soluble.

5. A process according to claim 4, in which the solvent is present at the time of addition of the base, thus forming a two-phase system.

6. A process according to claim 4, in which the solvent is added at the end of the precipitation of cerous carboxylate from the aqueous phase.

7. A process according to claim 4, in which hydrogen peroxide is added as an aqueous solution shortly after the addition of the base has been completed, and prior to the separation of the two layers, and the pH of the reaction mixture prior to the $H_2O_2$ addition is above 6.

8. A process according to claim 7 in which the addition of $H_2O_2$ is made after base is added in a stoichiometric amount according to the amount of total acid present.

9. A process according to claim 7 in which the addition of $H_2O_2$ is made only after at least nearly the entire stoichiometric amount of base corresponding to the amount of cerium has been added, and the pH of the reaction mixture has been adjusted to above 6.

10. A process according to claim 1 in which the amount of hydrogen peroxide is selected according to the extent desired of the conversion of cerous to ceric within the range from at least 5% to about 95%.

11. A process according to claim 10 in which there are at least two incremental additions of hydrogen peroxide, each incremental addition being followed by a heating-cooling sequence to decompose ceric-$H_2O_2$ complexes.

12. A process according to claim 1 in which the cerous carboxylate is prepared by adding an aqueous solution of hydrogen peroxide into an aqueous solution of alkali or ammonium carboxylate, followed by addition of an aqeuous solution of cerous salt, thereby forming the cerous carboxylate.

13. A process according to claim 12 which comprises adding an aqueous solution of hydrogen peroxide to the aqueous solution of cerous salt prior to the mixing with the alkali or ammonium carboxylate solution.

14. A process according to claim 12 which comprises adding an aqueous solution of hydrogen peroxide at a controlled rate during the mixing with the alkali carboxylate solution.

15. A process according to any one of claims 12, 13 or 14, carried out in the presence of an organic solvent to extract the ceric carboxylate as it is formed.

16. A process according to claim 1 carried out at a temperature within the range from room temperature up to 70° C.

17. A process according to claim 1 in which the cerous carboxylate is selected from the group consisting of cerous naphthenate, cerous 2-ethylhexoate, and cerous neodecanoate.

18. A process according to claim 1 in which the cerous carboxylate is derived from an aliphatic carboxylic acid.

19. A process according to claim 1 in which the water-immiscible liquid hydrocarbon solvent is selected from the group consisting of aliphatic, cycloaliphatic and aromatic hydrocarbon solvents having from about six to about fourteen carbon atoms.

20. A process according to claim 1, carried forward to an at least 5% conversion of cerous to ceric carboxylate.

21. A process according to claim 1, carried forward to a conversion within the range from 30% to 60% of cerous to ceric carboxylate.

22. A process according to claim 1, carried forward to a conversion within the range from 50% to 95% of cerous to ceric carboxylate.

* * * * *